United States Patent [19]

Djuric et al.

[11] Patent Number: 4,616,034
[45] Date of Patent: Oct. 7, 1986

[54] 15(R)-5-FLUOROPROSTACYCLINS, PHARMACEUTICAL COMPOSITIONS AND ANTI-THROMBOTIC METHOD OF USE THEREOF

[75] Inventors: Stevan W. Djuric, Evanston; Robert B. Garland, Northbrook, both of Ill.

[73] Assignee: G. D. Searle & Co., Skokie, Ill.

[21] Appl. No.: 706,806

[22] Filed: Feb. 28, 1985

[51] Int. Cl.⁴ ................. A61K 31/557; C07D 307/935
[52] U.S. Cl. ................... 514/469; 514/337; 549/465; 549/269
[58] Field of Search ........... 549/465; 546/269; 514/337, 469

[56] References Cited

U.S. PATENT DOCUMENTS 4,178,367 12/1979 Masaki et al. ............... 424/285
4,324,730 4/1982 Fried ............... 260/346.22
4,540,801 9/1985 Nysted et al. ............... 549/465

FOREIGN PATENT DOCUMENTS 0054795 6/1982 European Pat. Off. .
0062303 10/1982 European Pat. Off. .

OTHER PUBLICATIONS

Progress in Medicinal Chem., vol. 21 (1984), Chapter 6, pp. 238-279, by Whittle & Moncada.
Gandolfi et al, "Prostacyclin Analogs: Structure Activity Relationships", *Prostaglandins and Cardiovascular Disease*, Raven Press, New York, 1981, p. 184.
Flohe et al, Arzneim Forsch/Drug Res., 33(11), No. 9 (1983).

*Primary Examiner*—Henry R. Jiles
*Assistant Examiner*—Bernard I. Dentz
*Attorney, Agent, or Firm*—Stuart L. Melton

[57] ABSTRACT

The present invention provides novel compounds of Formula I

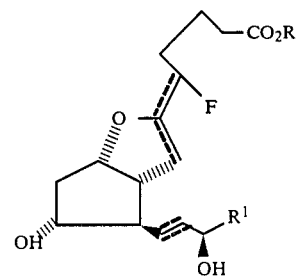

which are pharmacologically selectively useful as anti-thrombotic agents with minimal blood pressure lowering activity.

20 Claims, No Drawings

15(R)-5-FLUOROPROSTACYCLINS, PHARMACEUTICAL COMPOSITIONS AND ANTI-THROMBOTIC METHOD OF USE THEREOF

BACKGROUND OF THE INVENTION

The present invention relates to novel 15(R)-5 fluoroprostacyclins of Formula I

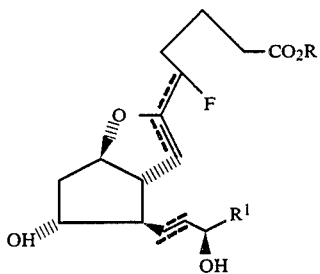

which, surprisingly, have been found to possess outstanding platelet aggregation inhibition activity without hypotensive effects at platelet aggregation inhibition (i.e., anti-thrombotic) doses.

The natural prostacyclin substance is a physiologically active substance of the formula

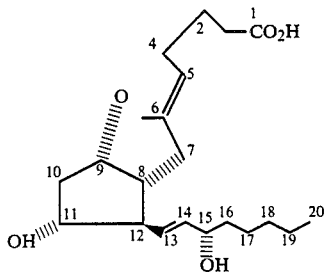

The shorthand designation of the compound is $PGI_2$ whereas the chemical name is (5Z)-9-deoxy-6,9α-epoxy-$\Delta^5$-$PGF_1$. See, for example, R. A. Johnson et al., *J. Am. Chem. Soc.* 99, 4182 (1977); R. A. Johnson et al., *Prostaglandins*, 12, 915 (1976); C. Pace-Asciak and L. S. Wolfe, *Biochemistry*, 10, 3657 (1971). The natural $PGI_2$ compound has a number of centers of chirality, including those at C-8, C-9, C-11, C-12 and C-15 carbon atoms. The hydroxy group at C-15 in the natural $PGI_2$ molecule lies below the plane of the cyclopentane ring with the ring substantially in the plane of the page. In the R,S priority designation system, the C-15 position is designated 15S in the natural $PGI_2$.

$PGI_2$ and related cyclic prostaglandins have been demonstrated to elicit a number of biological responses including, but not limited to, inhibition of blood platelet aggregation, lowering of blood pressure, stimulation or relaxation of smooth muscle, inhibition of gastric secretion and protection of gastric mucosa, induction of luteolysis, stimulation of uterine contraction, etc. See, for example, J. R. Vane et al., *Prostacyclin*, Raven Press, N.Y., 1979.

U.S. Pat. No. 4,178,367 discloses $PGI_2$ derivatives of the Formula:

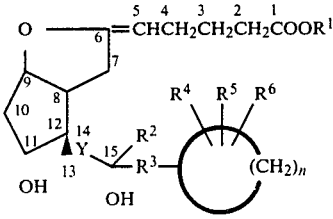

in which the wavy line attached to the carbon atom in the 15 position represents α or β configuration (i.e., S or R-configuration) or mixtures thereof. Accordingly, the carbon atom at C-15 may be designated as 15S or 15R. The patentees indicate that the above prostacyclin analogs possess pharmacological properties typical of prostaglandins in a selective fashion, in particular hypotensive activity, inhibitory activity on blood platelet aggregation, relaxing activity of artery, etc. Data are presented indicating that a 15S hydroxy derivative, specifically (5Z,13E)-(9α,11α,15S)-6,9-epoxy-11,15-dihydroxy-15-(3 propyl)cyclopentyl-16,17,18,19,20-pentanorprosta-5,13-dienoic acid methyl ester has greater blood pressure lowering activity compared to a 15R derivative, specifically, (5Z,13E)-(9α,11α,15R)-6,9 epoxy-11,15-dihydroxy-15-(1-butyl)-cyclobutyl-16,17,18,19,20 pentanorprosta-5,13-dienoic acid methyl ester. The data presented suggest that the 15R derivative is between about 10 and 25 times less active than the 15S compound indicated with respect to blood pressure lowering activity. With respect to blood platelet aggregation inhibition activity, the patentees indicate that the 15S-15-(3-propyl)(cyclopentyl) derivative demonstrates 50% inhibition of ADP-induced blood platelet aggregation at a concentration of 1.35 times $10^{-3}$ ug/ml. whereas the 15R-15-(1-butyl)cyclobutyl derivative produces 50% inhibition at a concentration of 4.2 times $10^{-3}$ μg/ml. From these data it is apparent that the 15S derivative is only very slightly more active than the 15R derivative with respect to in vitro inhibition of platelet aggregation.

There is no in vivo platelet aggregation inhibition data presented in the foregoing U.S. Pat. No. 4,178,367 from which one could draw any conclusions as to any differences in the separation of anti-aggregatory properties vs. hypotensive properties with respect to 15R or 15S derivatives. Further, it is noted that the 15R and 15S compounds discussed above are not otherwise structurally the same (i.e., different alkyl-cycloalkyl substituents are present at the 15 position) and, therefore, any differences in activities may be due to the influence of such different substituents. Moreover, the foregoing patent does not disclose any 5-fluoroprostacyclin derivatives. Inasmuch as the patentees indicate that the C-15 position may have either the R or S configuration or even mixtures thereof, it is evident that no therapeutic advantage is recognized or ascribed to either diastereomer over the other.

In a manner analogous to U.S. Pat. No. 4,178,367, Gandolfi et al., in discussing the structure-activity relationships among certain prostacyclin analogs, suggests that epimerization of the 15-hydroxy group, while compatible with the preservation of a certain anti-aggregatory activity, suppresses, at least in the anesthetized rat, the hypotensive effects. See Gandolfi et al., "Prostacyclin Analogs: Structure-Activity Relationships", *Prostaglandins and Cardiovascular Disease*, Raven Press, New York, 1981, page 184. The analogs described do not include any 5-fluoro derivatives. However, contrary to the foregoing publication, Flohe et al., in discussing structure-activity relationships of a series of prostacyclin analogs, state that as with natural prostacyclin, the carbon atom at C-15 has to be present in the S-configuration. See Flohe et al., Arzneim-Forsch/Drug Res., 33 (11) No. 9 (1983). In Table 4 of the foregoing publication, the authors compiled data on inhibition of in vitro platelet aggregation for representative pairs of antipodes and conclude that in all cases investigated, the S-isomer is more active than the R-isomer by roughly two orders of magnitude.

Halogenated $PGI_2$ derivatives have previously been proposed in order to enhance the stability of natural $PGI_2$. For example, European Patent Application Publication No. 0054795 discloses halogenated $\Delta^5$-prostacyclins, i.e., $PGI_2$, as well as halogenated $\Delta^6$-prostacyclins which are designated as $\Delta^6$-$PGI_1$ in this publication to distinguish from natural $PGI_2$-type prostacyclins when the double bond is present between the C-5 and C-6 positions. The foregoing publication excludes 5-monofluorinated $PGI_2$ compounds from within the scope of the disclosed invention. In discussing the various centers of chirality in the prostacyclin molecule, the inventors observe that there are two kinds of stereoisomers with regard to the asymmetric carbon atom at the 15-position in both the disclosed $PGI_1$ and $PGI_2$ structures and that the invention encompasses both possible stereoisomers as well as mixtures thereof. Accordingly, with respect to the C-15 carbon atom bearing the hydroxy group, it is evident that no distinction between 15R and 15S derivatives was made between these stereoisomers with respect to biological activity, stability or otherwise. Regarding biological activity presented in the foregoing European publication, 7-fluoro-$PGI_2$ sodium salt and 5-chloro-$PGI_2$ sodium salt were tested in comparison to natural $PGI_2$ with respect to hypotensive activity and both in vitro and extra vivo inhibitory activity of platelet aggregation, as well as activity in the inhibition of metastasis of malignant tumors. From the tests conducted, the inventors conclude that both the 7-fluoro and 5-chloro $PGI_2$ derivatives (sodium salts) have stronger activities with respect to the inhibition of platelet aggregation in comparison with their blood pressure lowering activities compared to $PGI_2$ (sodium salt) and therefore have higher selectivity of pharmacological activity than $PGI_2$. From the results obtained, the ratio of blood pressure lowering activity (effective dose causing a 20% lowering of the mean blood pressure) and the platelet aggregation inhibiting activity (minimum concentration to obtain 50% inhibition of platelet aggregation) was calculated. These data indicate that $PGI_2$ has an effective ratio of 1 whereas the 7-fluoro derivative has a ratio of 32 and the 5-chloro derivative has a ratio of 4.

U.S. Pat. No. 4,324,730 discloses prostaglandin and prostacyclin compounds wherein a fluorine atom may be substituted in any one or more of the 4,4;7,7;10,10; and 5 positions. The foregoing patent pertains only to $\Delta^5$-prostacyclins, i.e., $PGI_2$. Although a general reaction scheme is proposed, no specific method for the preparation of a 5-monofluorinated $PGI_2$ compound is disclosed. Also, the only statement made with respect to stereoisomers is that appended moieties may be either in the α or β stereochemical configuration in the molecule and no distinction or preference is noted for either stereochemical configuration and, further, no specific biological test data are presented.

European Patent Application (Publication No. 062303, Oct. 13, 1983), assigned to the assignee of this invention, discloses 5-fluoro prostacyclins, including 5,6- or 6,7-unsaturated derivatives thereof along with the process for their preparation. The foregoing published application does not detail the stereochemistry of the 5-position fluoro group or the 15-hydroxy group.

In contrast to the research conducted heretofore, applicants have focused on the potential significance of the specific stereochemistry at the C-15 carbon atom of the prostacyclin structure and have, surprisingly, found that in spite of the absence of any reported distinction or preference in the prior art, that the stereochemistry at the C-15 position is determinative of outstanding in vivo biological properties. More specifically, it has now been found that compounds of Formula I wherein the hydroxy substituted carbon atom at the 15-position is in the R configuration, coupled with the presence of a fluoro group in the C-5 position possess valuable platelet aggregation inhibition properties while at the same time demonstrate virtually no blood pressure lowering effects, thereby providing for the first time a selective therapeutic anti-aggregatory effect in a stabilized cyclic prostaglandin.

DETAILED DESCRIPTION OF THE INVENTION

Accordingly, the foregoing advantages of the present invention are achieved by providing a 5-fluoro,15(R)-hydroxy prostacyclin of Formula I

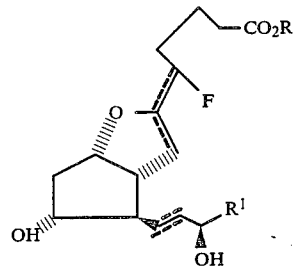

wherein R represents hydrogen, lower alkyl, or a pharmaceutically acceptable cation;

R¹ represents a straight or branched chain alkyl group of 1 to 5 carbon atoms, a hydrocarbon group of 1 to 5 carbon atoms optionally containing 1 to 2 double bonds or 1 ethynyl group; a cycloalkyl group of 3 to 7 carbon atoms; phenyl; or pyridyl;

the symbol ════ between the 5-, 6- and 7-positions indicates that a single or double bond exists between either the 5- and 6-positions or the 6- and 7-positions; and the symbol ════ between the 13- and 14-positions indicates that a single, double or triple bond exists between the 13- and 14-positions.

In the above Formula, when the double bond is present between the 6- and 7-positions, the stereochemistry of the fluoro substituted 5-position may be either R or S, with R being preferred.

When the bond between the carbon atoms at the 13- and 14-positions is a double bond, the compounds include the cis- or trans-isomers or a mixture thereof, the trans-isomer being preferred.

When the double bond is present between the 5- and 6-positions, E and Z stereoisomerism exists and either possibility is within the scope of the present invention. The presently preferred compounds of Formula I are the 5(E) isomers.

Examples of suitable R alkyl groups are lower alkyl groups of 1 to 6 carbon atoms including methyl, ethyl, n-propyl, isopropyl, n-butyl, n-hexyl, etc.

Exemplary of suitable pharmaceutically acceptable salts are potassium, sodium, calcium, barium or any other cation capable of reacting with the C-1 carboxylic acid moiety provided same does not adversly affect the pharmacological properties of the resulting compound.

Examples of $R^1$ cycloalkyl groups include, cyclopropyl, cyclobutyl, cyclopentyl, cyclohexyl, cycloheptyl and the like.

Examples of suitable hydrocarbon groups within the definition of the $R^1$ group include the alkyl groups corresponding to R as well as alkenyl and/or alkynyl moieties which may be either straight or branched chain. Especially preferred compounds within the scope of Formula I are the compounds of Formulas I-A, B and C.

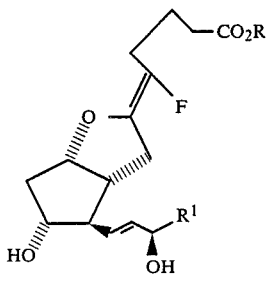

(A)

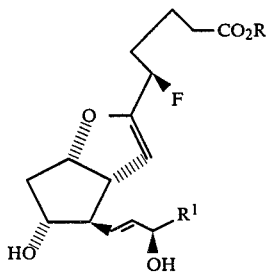

(B)

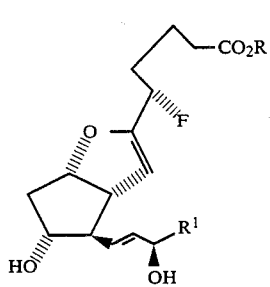

(C)

A specifically preferred embodiment is the compound of Formula I-D.

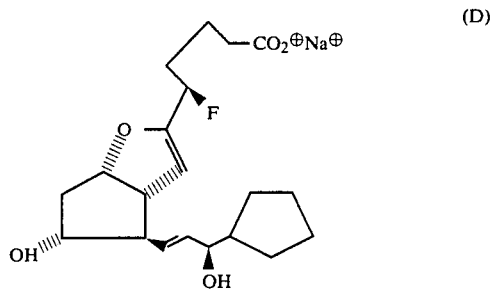

(D)

The compounds of Formula I are specifically useful as blood platelet anti-aggregation agents, i.e., antithrombotic agents, for ultimate use in the treatment, prevention or prophylaxis of thrombus formation and cardiovascular diseases or conditions such as atherosclerosis, arteriosclerosis and myocardial infarcts. The compounds of the present invention may also be used as additives for preventing platelet aggregation in whole blood, e.g., for storage purposes, as well as in hemodialysis and surgery.

The compounds of the present invention may be administered in such oral dosage forms as tablets, capsules, pills, powders, granules, elixirs or syrups. Likewise, they may be administered intravascularly, intraperitoneally, subcutaneously or intramuscularly using forms known to those of ordinary skill in the pharmaceutical arts. Typically, the preferred form of administration is oral. An effective, but non-toxic amount of the compound is employed to obtain the desired blood platelet anti-aggregation effect. The dosage regimen utilizing the compounds of the present invention is selected in accordance with a variety of factors including the type, age, weight, sex and medical condition of the patient; the severity of the condition to be ameliorated; the route of administration; and the particular compound employed or mixtures thereof. A physician of ordinary skill can readily determine and prescribe the effective amount of the drug required to prevent, treat or arrest the progress of the condition being treated. The compounds of the present invention may be administered in single or divided doses as required. Although the exact dose must be individually titrated, typically the preferred dosage range will vary between about 0.001 to about 10 mg/kg/day and, most preferably between about 0.005 to about 5 mg/kg/day.

In the blood platelet anti-aggregation inhibition pharmaceutical compositions and methods of the present invention, the foregoing active ingredients will typically be administered in mixture with suitable pharmaceutical excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug components may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like. Likewise, where appropriate, the compounds of the invention may be formulated for parenteral administration.

The compounds of the present invention may be prepared in accordance with the following general reaction scheme:

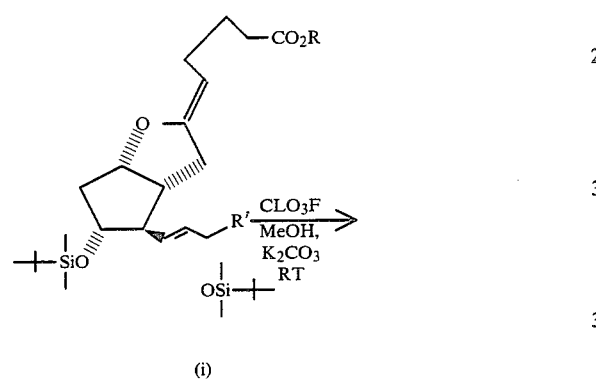

(i)

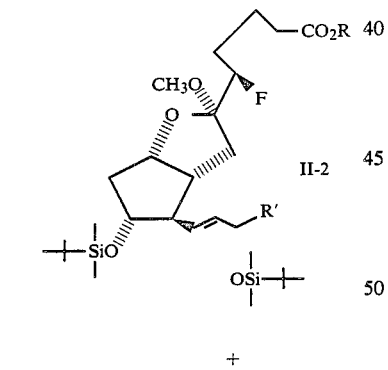
II-2

+

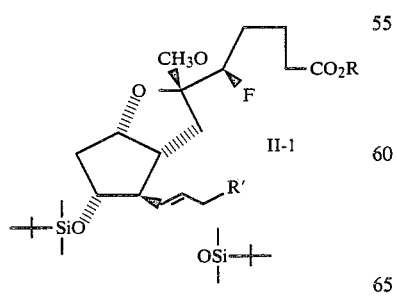
II-1

+

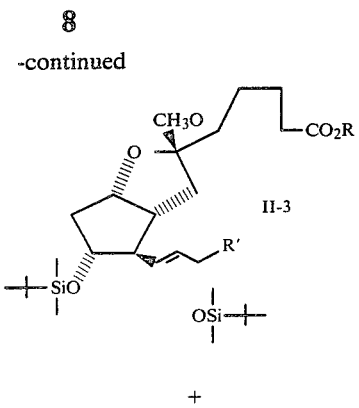
II-3

+

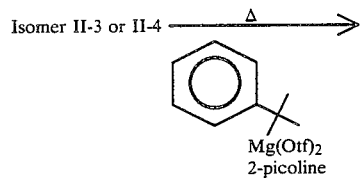
II-4

Isomer II-3 or II-4 $\xrightarrow{\Delta}$ 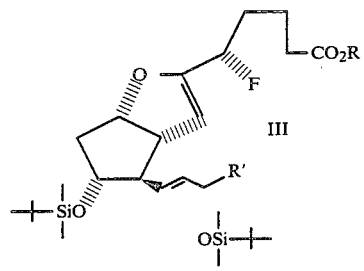 Mg(OTf)$_2$ 2-picoline

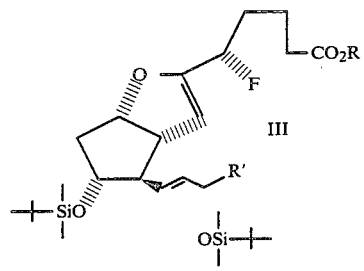
III

Isomer II-1 or III-2 $\xrightarrow{\Delta}$ Mg(OTf)$_2$ 2-picoline

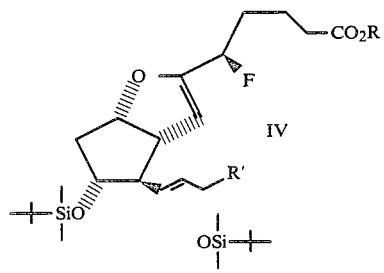
IV

+

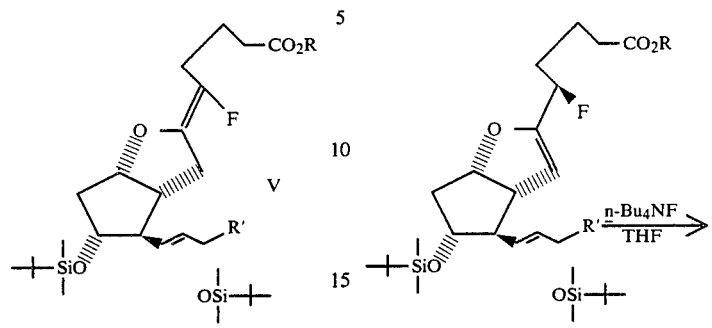
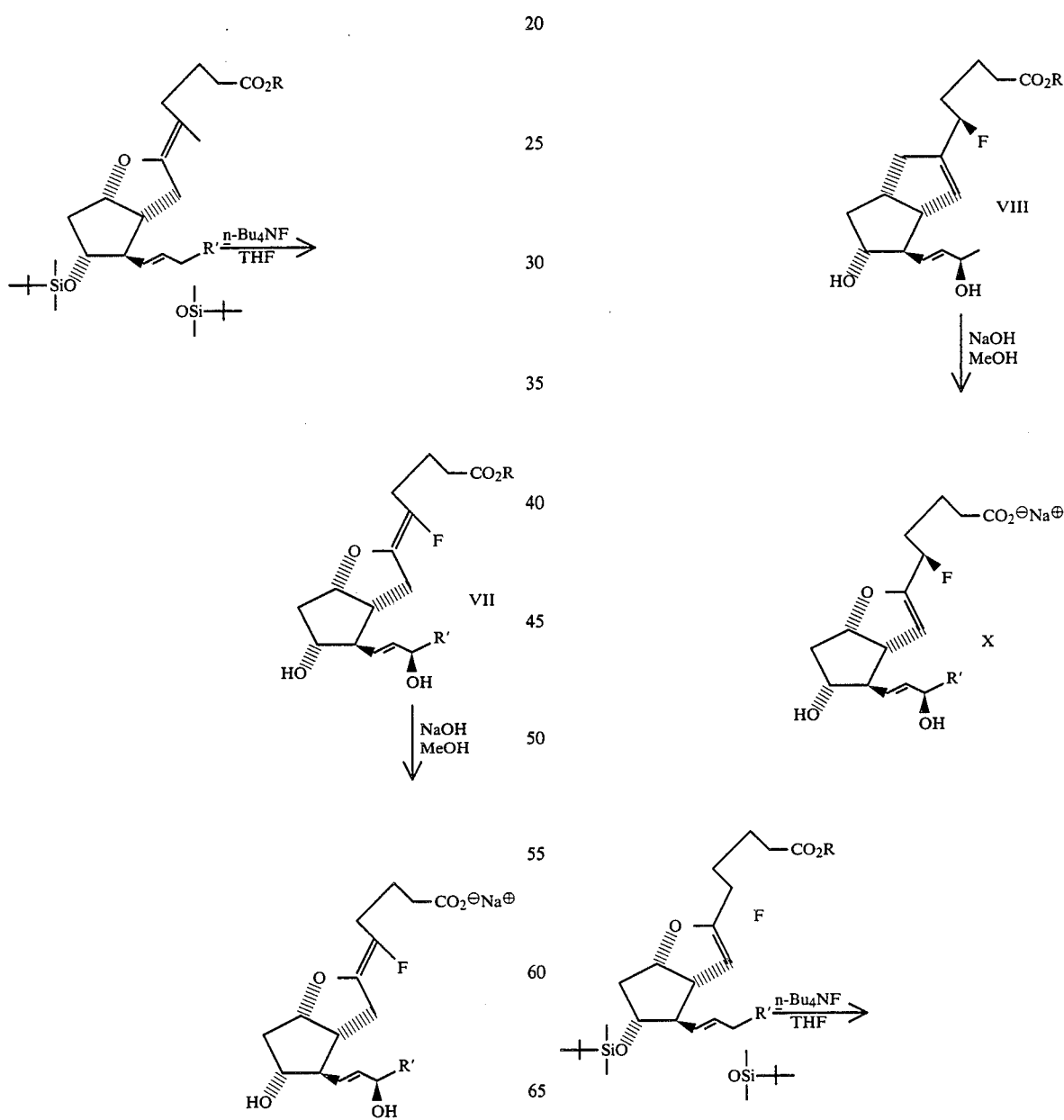

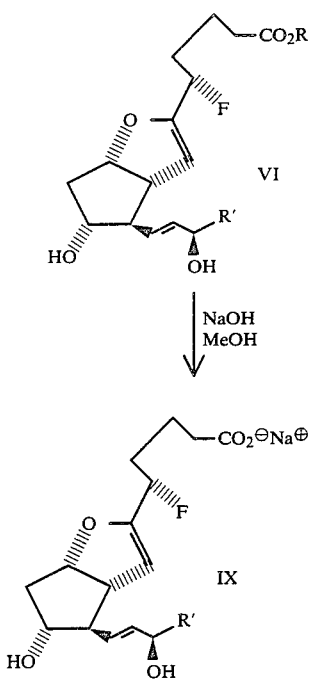

The starting materials for the synthesis of 15(R or S),5-fluoroprostacyclin analogs, i.e., compounds of Formula (i) are prepared in accordance with the procedures previously described in the literature with appropriate selection of R and $R^1$ substituents corresponding to those of Formula I of the present invention. See, for example, U.S. Pat. No. 4178367, European Patent Publication No. 0054795 and Publication No. 062303 for suitable starting materials, reaction conditions and epimerizatin methods for the synthesis and isolation of 15R and 15S hydroxy derivatives.

As depicted in the foregoing general reaction scheme, a suitably protected prostacyclin analog such as (i) wherein R is preferaby a lower alkyl group (e.g. methyl) is treated with gaseous perchloryl fluoride in a solvent such as methanol containing an excess of soluble or suspended base such as anhydrous potassium carbonate, sodium carbonate, or cesium carbonate. This reaction gives rise to four isomeric methoxy-fluoro PGI derivatives. The isomers can be separated by exhaustive chromatography on a suitable adsorbent such as Woelm TM silica gel or Florisil TM preconditioned with a base, such as triethylamine. Thermolytic elimination of alcohol from the individual isomers or mixtures of II-3 and 4 and II-1 and 2 in a high boiling inert solvent such as xylene or tert-butylbenzene in the presence or absence of a catalyst such as magnesium triflate (Lewis acid type) and a high boiling nucleophilic base such as 2-picoline affords the 5(R)-$\Delta^6$-fluoro $PGI_1$ derivative (III) or the
5(S)-Fluoro-$\Delta^6$-$PGI_1$ derivative (IV) and the
5-fluoro-$PGI_2$ derivative (V).

Isomers (IV) and (V) can be separated by column chromatography on a suitable absorbent such as Woelm TM silica gel or Florisil TM preconditioned with a base such as triethylamine.

Isomers (III), (IV), and (V) can each be taken individually and treated with a fluoride source such as tetrabutylammonium fluoride in tetrahydrofuran (in the cases where the 11,15 protecting groups are trialkylsily) to provide the prostacyclin analogs (VII), (VIII) and (VI). To convert these compounds, in which R of the general formula is alkyl, to pharmaceutically acceptable salts they may then be treated with an appropriate base such as sodium hydroxide to afford (IX) and (X). Other bases such as potassium hydroxide or calcium hydroxide may be employed to obtain the corresponding $K^+$ or $Ca^{++}$ salts. Likewise $NH_4^+$ or other quaternary ammonium salts may be prepared using, for example, tetramethyl ammonium, diethyl ammonium, benzyl ammonium, etc. These salts are routinely stored under anhydrous condition at temperatures between 0° C. and 26° C. and are dissolved in the appropriate vehicle for biological testing (e.g. neutral pH buffer, saline) when necessary.

The following information with respect to reagents, chromatographic procedures and analytical methods are noted in conjunction with the above general reaction scheme and description to further clarify the process for preparing the compounds of the invention.

Reagents: methanol was freshly distilled from magnesium methoxide. Potassium carbonate was dried at 80° C. under high vacuum for 2 hrs. Perchloryl fluoride was measured as a liquid by condensation in a graduated centrifuge tube cooled in a dry ice—acetone bath. It was added by means of a tube just below the liquid surface of the reaction. The rate of addition was controlled by gradually raising the tube from the cooling bath.

Chromatography: MPLC (medium pressure liquid chromatography) except where noted was run on a Woelm TM silica gel column 25 mm×1 m which had been prewashed with 95:5 ethyl acetate—triethylamine (500 ml). Then to the solvent system (500 ml) which is given as a percentage of ethyl acetate in hexane, about 0.2% triethylamine was added to each solvent mixture. Where two concentrations are given a step gradient elution was employed. The column was regenerated by washing with a small amount of ethyl acetate then with 500 ml of ethyl acetate which had been saturated with water. About 1% triethylamine was added to each solvent mixture. TLC monitoring was carried out using coated plastic plates developed with 10% ethyl acetate in hexane for silylated products and pure ethyl acetate for deprotected products. For distinction of the isomeric products generally a multiple development (3 to 6 times) on 20 cm plates was employed. In this manner all of the isomers could be distinguished especially in column fractions even when the Rf's for a single development were essentially the same.

$^1$H and $^{13}$C NMR spectra were recorded on a Varian FT80 or XL200 spectrometer at 80 or 200 MHz (for $^1$H) and 50.3 MHz (for $^{13}$C) with chemical shifts reported in parts per million ($\delta$) downfield from tetramethylsilane as an internal standard. Splitting patterns are designated as s, singlet; d, doublet; t, triplet; q, quartet; and m, multiplet.

Infra red spectra (IR) were obtained as solution in chloroform ($CHCl_3$) and are given in $cm^{-1}$. (Only major frequencies are recorded.) Mass Spectra were run on a Kratos MS30 or MS50 at 70 ev and an ionising current of 300 MA.

Elemental analyses were performed by microanalytical procedures.

The following non-limiting examples further illustrate details for the preparation of compounds of the present invention. The invention as a whole is not to be construed or limited either in spirit or in scope by the following examples. Those skilled in the art will readily understand the variations in the conditions and processes exemplified in the following preparative procedures can be utilized to prepare these compounds. All temperatures are degrees Celcius unless otherwise specified.

EXAMPLE 1

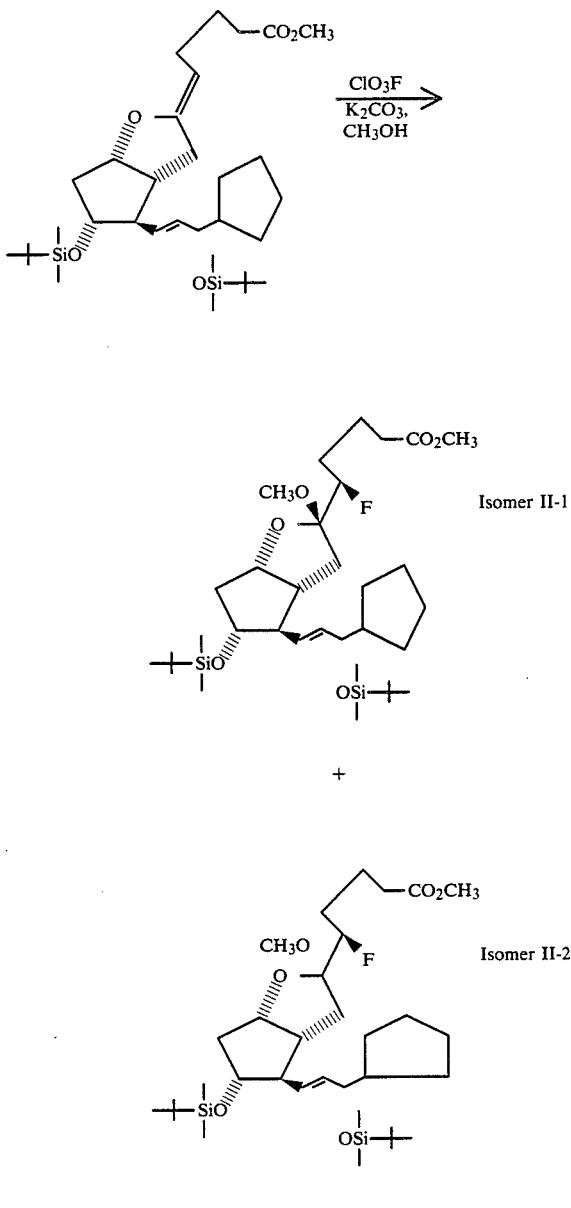

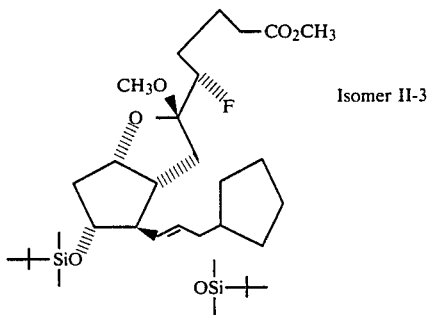

+

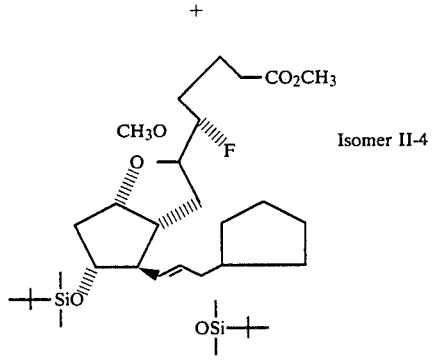

Preparation of
II-1. Methyl 11α,15R-bis[[(1,1-dimethylethyl)dimethylsilyl]oxy]-15-cyclopentyl-6,9α-epoxy-5R-fluoro-6S-methoxy-16,17,18,19,20-pentanorprost-13E-en-1-oate.
II-2. Methyl 11α,15R-bis[[(1,1-dimethylethyl)dimethylsilyl]oxy]-15-cyclopentyl-6,9α-epoxy-5R-fluoro-6R-methoxy-16,17,18,19,20-pentanorprost-13E-en-1-oate.
II-3. Methyl 11α,15R-bis[[(1,1-dimethylethyl)dimethylsilyl]oxy]-15-cyclopentyl-6,9α-epoxy-5S-fluoro-6S-methoxy-16,17,18,19,20-pentanorprost-13E-en-1-oate.
II-4. Methyl 11α,15R-bis[[(1,1-dimethylethyl)dimethylsilyl]oxy]-15-cyclopentyl-6,9α-epoxy-5S-fluoro-6R-methoxy-16,17,18,19,20-pentanorprost-13E-en-1-oate.

A mixture of 1.64 g of (i), 2.20 g of potassium carbonate and 40 cm$^3$ of methanol was stirred under nitrogen at 15° C. while perchloryl fluoride (1.0 cm$^3$) was added over 30 minutes. The cooling bath was removed and the mixture was stirred for an additional 30 minutes. The mixture was diluted with 200 cm$^3$ of ice-water and extracted with hexane. The organic extracts were combined and washed with water and brine, dried over sodium sulfate and evaporated in vacuo. The crude product (1.8 g) was chromatographed repeatedly using MPLC (Ethyl acetate:hexane:triethylamine 2.5:97:0.5) until all four isomeric products were obtained pure. Thus obtained were (in order of decreasing Rf)
Isomer II-4 150 mg
Isomer II-2 265 mg
Isomer II-1 820 mg
Isomer II-3 460 mg   Total yield 1.695 g
Spectral data
NMR: ($^1$H, δ, CDCl$_3$, 200 MHz) 0.03 (12H, d, Si(CH$_3$)$_2$), 0.85 (18H, d, Si t-Bu) 1.2–2.6 (20H, m cylcoalkyl Hs and α-chain Hs), 3.7–3.8 (3H, s, CO₂CH₃), 3.8–3.9 (2H, m, CH-OSit-BuMe₂), 4.4–4.7 (2H, m, CH-F and C-9 H), 5.45 (2H, m, C-13, 14 olefinic Hs).

Shift of 6-OCH₃ methyl in ¹H NMR. Isomer II-1, δ=3.32, Isomer II-2, δ=3.33, Isomer II-3, δ=3.22, Isomer II-4, δ=3.37.

IR (CHCl₃): 2950, 1730, 1435, 1250, 850 cm⁻¹ MS (High Resolution, EI): 585, 553, 535, 509, 479, 443, 409, 363, 327, 265, 213, 171, 147, 117, 73. C₃₀H₅₄O₆FSi₂ (M⁺-t-Bu) requires 585.3444. Found 585.3444. Deviation 0.0 ppm.

EXAMPLE 2

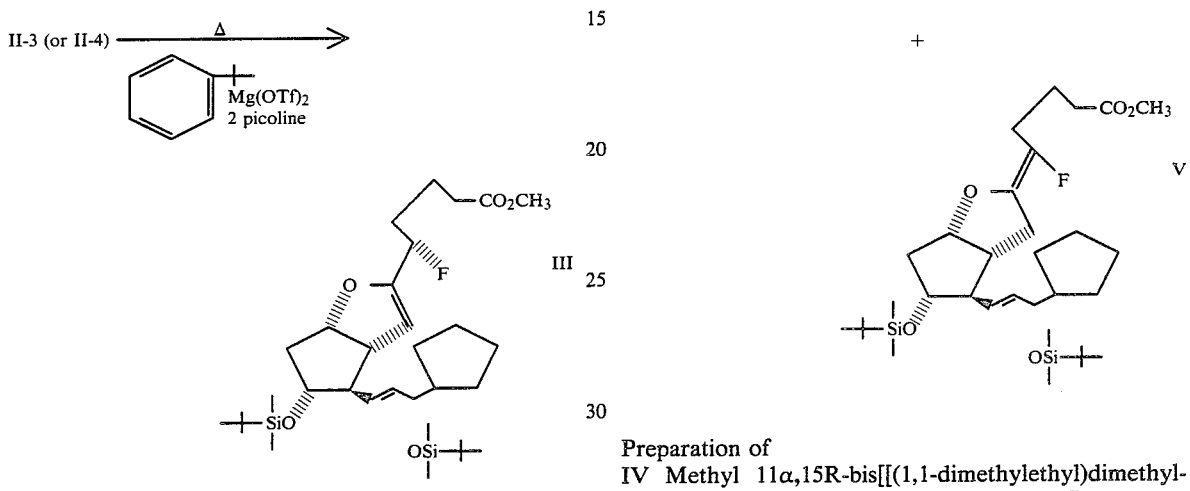

Preparation of
III-Methyl 11α,15R-bis[[(1,1-dimethylethyl)dimethylsilyl]oxy]-15-cyclopentyl-6,9α-epoxy-5S-fluoro16,17,18,19,20-pentanoprosta-6,13E-dien-1-oate.

To a solution of 655 mg of II-3 in 15 cm³ of tertbutylbenzene was added 4 drops of 2-picoline and 5 mg of magnesium triflate. The mixture was thoroughly flushed with argon and then heated at reflux temperature for ½ hour. The cooled mixture was filtered through sintered glass and the solvents removed from the filtrate under nitrogen. MPLC (EA:hexane:Et₃N, 96.5:3:0.5) of the residue provided 495 mg of the title compound (III) followed by 34 mg of recovered II-3.

Spectral data
NMR (¹H, δ, CDCl₃, 200 MHz): 0.02 (12H, d, SiMe₂), 0.86 (18H, d, Sit-Bu), 1.18–2.6 (18H, m, cycloalkyl and α-chain Hs), 2.9 (1H, m, C-8H), 3.66 (3H, s, Co₂CH₃), 3.75–3.85 (2H, m, CH-OSitBuMe₂), 4.8–5.0 (2H, m, CH-F and C-9H), 5.02 (1H, m, C-7H), (5.38–5.6 (2H, m, C-13,14 olefinic Hs) IR (CHCl₃): 2850, 1735, 1670, 1465, 1250, 850 cm⁻¹ MS (High Resolution, EI): 591, 590, 553, 535, 437, 409, 391, 265, 169, 73. C₂₉H₅₀O₅Si₂F (M⁺-t-Bu) requires 553.3182. Found 553.3182. Deviation in p.p.m. 0.0.

EXAMPLE 3

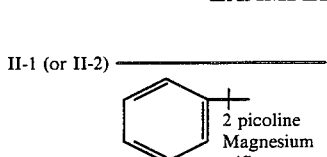

-continued

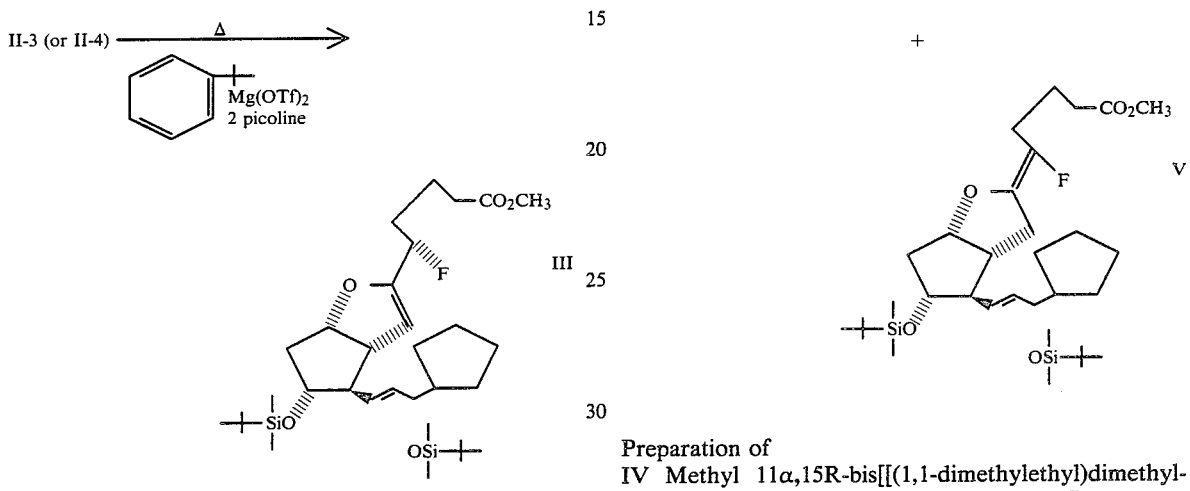

Preparation of
IV Methyl 11α,15R-bis[[(1,1-dimethylethyl)dimethylsilyl]oxy]-15-cyclopentyl-6,9α-epoxy-5R-fluoro-16,17,18,19,20-pentanorprosta-6,13E-dien-1-oate.
and
V Methyl 11α,15R-bis[[(1,1-dimethylethyl)dimethylsilyl]oxy]-15-cyclopentyl-6,9α-epoxy-5-fluoro-16,17,18,19,20-pentanorprosta-5E,13E-dien-1-oate.

To a solution of 358 mg of II-1 in 10 cm³ of tert-butylbenzene was added 2 drops of 2-picoline and 5 mgs of magnesium triflate. The mixture was thoroughly flushed with argon and heated at reflux temperature (mag. stirring) for 20 minutes. The cooled reaction mixture was filtered through sintered glass and the solvent removed under nitrogen. The residue was chromatographed using MPLC (EA:hexane:Et₃N,1.5:98:0.5). Mixed fractions were rechromatographed until the isomers were pure as determined by NMR.

Thus obtained were
10 mg of V
230 mg of IV
23 mg of recovered II-1
Spectral data
IV:
NMR (¹H, δ, CDCl₃ 200 MHz): 0.02 (12H, d, SiMe₂), 0.86 (18H, d, Sit-Bu), 1.18–2.6 (18H, m, cycloalkyl and α-chain Hs), 2.9 (1H, m, c-8H), 3.66 (3H, s, CO₂CH₃) 3.75–3.85 (2H, m, H-C-OSit-BuMe₂), 4.8–5.0 (2H, m, CH-F and C-9H), 5.02 (1H, m, C-7H), 5.38–5.6 (2H, m, C-13,14 olefinic Hs) IR (CHCl₃): 2850, 1735, 1670, 1465, 1250, 850 cm⁻¹

V:
NMR (¹H, δ, CDCl₃, 200 MHz): 0.02 (12H, d, SiMe₂), 0.85 (18H, d, Sit-Bu), 1.2–2.65 (20H, m, cycloalkyl Hs, α-chain Hs, C-8H), 3.66 (3H, s, CO₂CH₃), 3.8–3.9 (2H, m, H-C-OSit-BuMe₂), 4.55 (1H, m, C-9H), 5.4–5.6 (2H, m, olefinic Hs).

NMR ($^{13}$C, δ, CDCl$_3$, 50.3 MHz): 173.9 (C=O), 142.6 (C5, J-222H$_z$) 141.8 (C6,J-47H$_z$) 26.7 (C4,J=25H$_z$). IR (CHCl$_3$): 2900, 1732, 1660, 1470, 1250, 850 cm$^{-1}$

MS (High Resolution, EI): 610, 553, 535, 437, 409, 391, 327, 265, 213, 171, 149, 73. C$_{33}$H$_{59}$O$_5$F$_1$Si$_2$ requires 610.3884. Found 610.3888. Deviation 0.4 ppm.

EXAMPLE 4

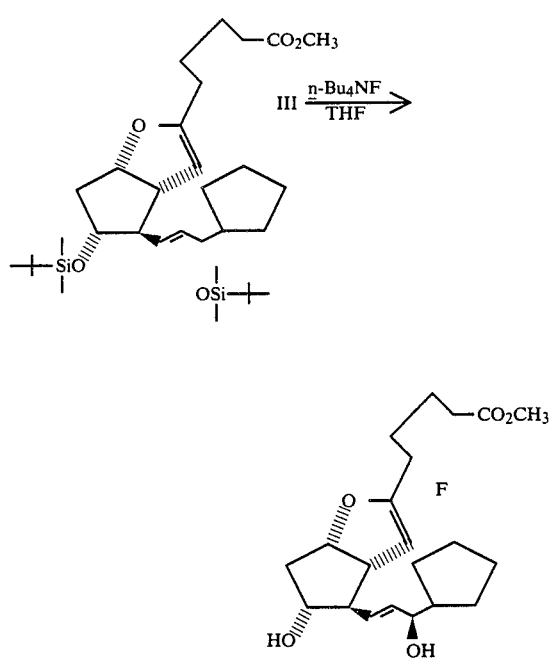

Preparation of

VI Methyl 15-cyclopentyl-6,9α-epoxy-5S-fluoro-11α,15R-dihydroxy-16,17,18,19,20-pentanorprosta-6,13E-dien-1-oate.

Compound III (0.17 g, 0.16 mMol) was dissolved in 3 cm$^3$ of dry tetrahydrofuran containing 5 equivalents of tetra n-butylammonium fluoride. The mixture was stirred for 10 hours at 26° C. under argon, and then partitioned between ether and water. The organic layer was separated, dried (Na$_2$SO$_4$) and evaporated. The crude product was purified by chromatography on Florisil TM (EA:hexane:Et$_3$N,50:49:1). Thus obtained was 67 mg of material (57%).

Spectral data

NMR ($^1$H, δ, CDCl$_3$, 80 MHz): 1.2–2.6 (20H, m, cycloalkyl Hs, α-chain Hs), 3.0 (1H, m, C-8H), 3.66 (3H, s, CO$_2$CH$_3$), 3.75 (2H, m, CH-OH), 4.6–4.8 (2H, m, CH-F and C-9H), 5.0 (1H, m, C-7H), 5.3–5.6 (2H, m, C-13,14 olefinic Hs)

IR (CHCl$_3$): 3600–3450, 1735, 1670, 1465 cm$^{-1}$ MS (High Resolution, EI): 382, 275, 247, 194, 121, 97. C$_{21}$H$_{31}$O$_5$F requires 382.2151. Found 382.2160. Deviation 0.9 ppm.

EXAMPLE 5

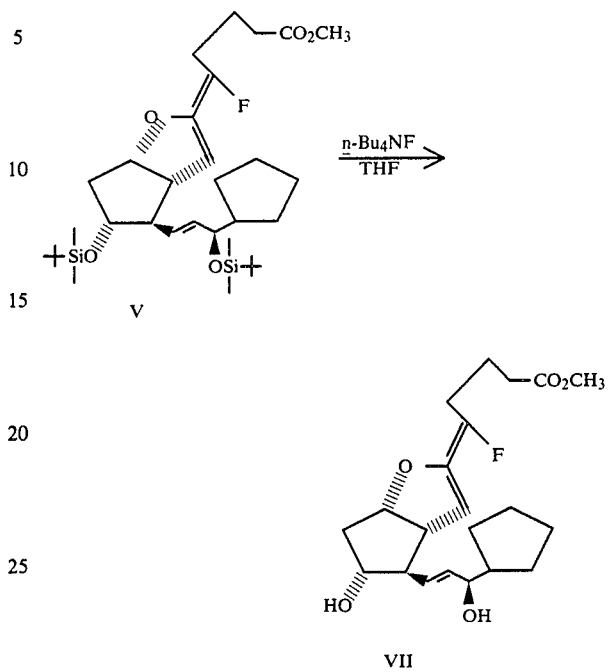

Preparation of

VII Methyl 15-cyclopentyl-6,9α-epoxy-5-fluoro-11α,15R-dihydroxy-16,17,18,19,20-pentanorprosta-5E,13E-dien-1-oate.

Compound V (5 mg) was dissolved in 2 cm$^3$ of dry tetrahydrofuran containing excess tetra n-butylammonium fluoride (1 cm$^3$ of a 1M solution in THF). The mixture was stirred for 10 hours under argon at 26° C. and then partitioned between saturated sodium bicarbonate solution and ethyl acetate. The organic layer was separated, washed with brine and then dried (Na$_2$SO$_4$).

Evaporation of the volatiles in vacuo afforded 9 mg of crude product. Chromatography on Merck silica gel 60 (EA:hexane:Et$_3$N, 50:50:1→90:10:1) afforded 1:0 mg of product.

Spectral data

NMR ($^1$H, δ, CDCl$_3$, 80 MHz): 1.2–2.6 (20H, m, cycloalkyl Hs, α-chain Hs, C-8H), 3.66 (3H, s, CO$_2$CH$_3$), 3.8 (2H, H-C-OH), 4.5 (1H, m, C-9H), 5.4–5.6 (2H, m, C-13,14 olefinic Hs). IR (CHCl$_3$): 3600–3450, 2900, 1732, 1660 cm$^{-1}$.

EXAMPLE 6

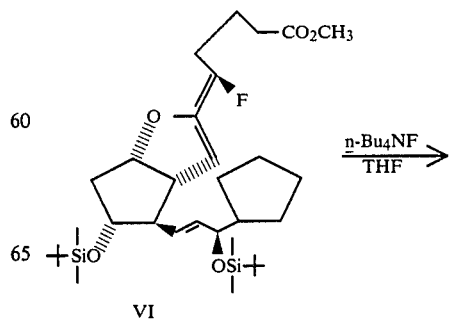

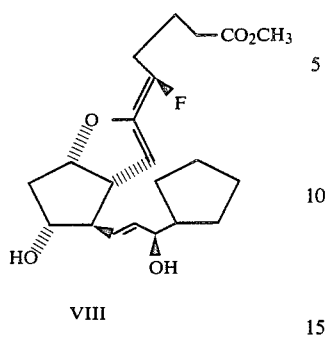

VIII

Preparation of

VIII Methyl 15-cyclopentyl-6,9α-epoxy-5R-fluoro-11α,15R-dihydroxy-16,17,18,19,20-pentanorprosta-6,13E-dien-1-oate Compound IV (0.6 g, 1 mMol) was dissolved in dry tetrahydrofuran (5 cm³) containing 3.0 cm³ of a 1M solution of tetra n-butylammonium fluoride in THF. The mixture was stirred magnetically under argon for 10 hours at 20° C. and then the majority of solvent removed under nitrogen. The residue was partitioned between 2N sodium bicarbonate and ethyl acetate and the organic layer separated and washed with brine. Evaporation of the dried ($Na_2SO_4$) solvent in vacuo afforded a crude product (1.0 g) which was purified by chromatography on Florisil (EA:hexane:$Et_3N$ 50:49:1→90:9:1). Thus obtained was 350 mg of the title compound as an oil.

Spectral data

NMR ($^1$H, δ, $CDCl_3$, 80 MHz): 1.25–2.75 (20H, m, cycloalkyl Hs, α-chain Hs), 3.00 (1H, m, C-8H), 3.7 (3H, s, $CO_2CH_3$), 3.75 3.9 (2H, m, C$\underline{H}$-OH), 4.6–5.2 (2H, m, C$\underline{H}$-F and C-9H), 5.1 (1H, m, C-7H) 5.4–5.6 (2H, m, C-13,14 olefinic Hs).

IR ($CHCl_3$): 3600–3450, 2900, 1735, 1670 cm$^{-1}$

MS (High Resolution, EI): 382, 275, 247, 194, 121, 99. $C_{21}H_{31}FO_5$ requires 382.2146. Found 382.2162. Deviation 1.6 ppm.

EXAMPLE 7

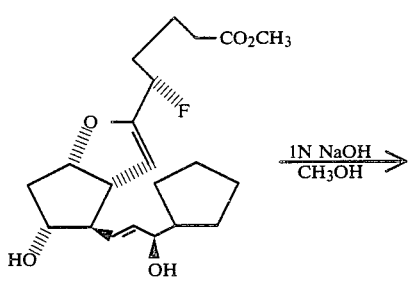

VI

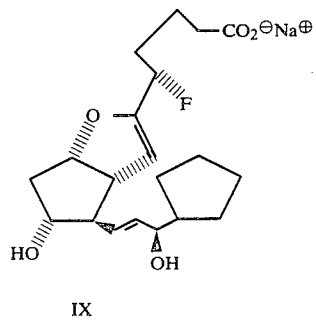

IX

Preparation of

IX  15-cyclopentyl-6,9α-Epoxy-5S-fluoro-11α,15R-dihydroxy-16,17,18,19,20-pentanorprosta-6,13E-dien-1-oic acid, sodium salt.

Compound VI (70 mg) was dissolved in a minimum amount of methanol and the solution cooled in ice. 0.25 cm³ of 1N sodium hydroxide was added via a syringe and the mixture stirred at 26° C. for 10 hours. At this point, the solvent was removed under nitrogen and the residue dried under high vacuum for 5 hours. Thus obtained was 52 mg of the title compound as an amorphous solid. This material was used as such for biological assay.

EXAMPLE 8

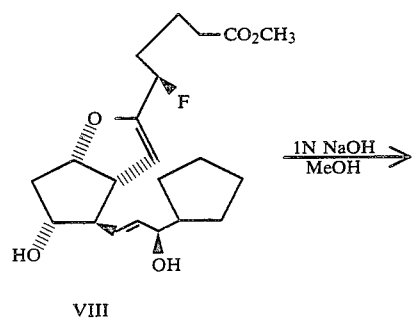

VIII

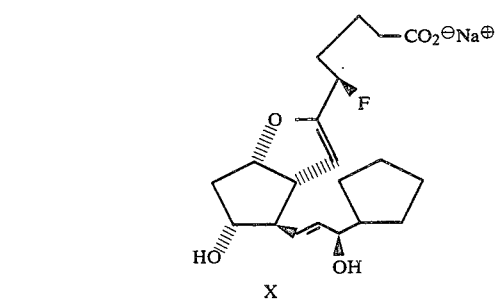

X

Preparation of

X 15-cyclopentyl-6,9α-Epoxy-5R-fluoro-11α,15R-dihydroxy-16,17,18,19,20-pentanorprosta-6,13E-dien-1-oic acid, sodium salt.

Compound VIII (0.23 g, 0.61 mMol) was saponified in the manner described for Example 7. Thus obtained was 195 mg of the title compound as an amorphous solid. This material was used as such for biological assay.

The compounds of the present invention were tested in accordance with standard laboratory procedures to determine their platelet anti-aggegatory and hypotensive characteristics, both in vitro and in vivo.

The test procedures utilized are as follows:

PLATELET ANTI-AGGREGATORY ACTIVITY

In vitro ADP aggregation

Rationale: The changes in optical density resulting from ADP-stimulation of platelet-rich plasma is used to identify compounds which inhibit or reverse platelet activation.

Description:
1. Platelet-rich plasma (PRP) is obtained from citrated whole rate blood.
2. Compound solutions are prepared at the initial screening dose of $1 \times 10^{-4}$M.
3. The prostacyclin (PGI$_2$) standard is prepared in 0.1M NaOH-glycine (pH 10.0) over a range of $10^{-9}$–$10^{-8}$M.
4. ADP in saline is added to PRP over a range of 1–2 uM to determine a concentration eliciting maximum aggregation within one minute.
5. PRP containing standard or test compound is preincubated for 1 minute and then stimulated with ADP. Vehicle controls are tested simultaneously.
6. The aggregation wave generated is monitored until the reversal phase is observed.
7. Platelet aggregation is quantified as the units of depth between the baseline and maximum depth.
8. Dose-response curves are generated for percent inhibition of ADP-induced platelet aggregation.
9. In vitro activity of the compounds screened is assessed by comparison of IC$_{50}$ (M) with that of PGI$_2$.
10. Compounds with IC$_{50}$'s less than or equal to $1 \times 10^{-4}$M are designated "active."

In vivo ADP-thrombocytopenia

Vehicle/compound in saline is infused for five minutes in the right jugular vein of rats (400–500 g) anesthetized with pentobarbital. Adenosine diphosphate (0.5 mg/kg) in saline is immediately infused for one minute in the left jugular vein. Blood samples are drawn (1:10 into 3.8% citrate) and platelets counted on a Coulter counter and platelet numbers in treated animals are compared to controls. The ED$_{50}$ (effective dose in 50% of treated animals-μg/kg/minute) for compound activity is calculated from linear regression.

HYPOTENSIVE ACTIVITY

Hexamethonium Rat (Duration)

Spontaneously hypertensive rats (300–400 g.) are anesthesized with 100 mg/kg barbital/25 mg/kg pentobarbital ip. The jugular vein and carotid artery are then cannulated with polyethylene-50 tubing (for drug administration and blood pressure measurement, respectively). A tracheotomy tube is inserted and animals breathe 100% O$_2$ spontaneously. Body temperature is maintained at 37° C. with a thermister probe and heat lamp. Rats are then dosed with 1 mg/kg hexamethonium, iv bolus. After a 10-minute stabilization period, animals are dosed with compound. All compounds are dissolved in either glycine buffer or saline and given in a volume of 1 ml kg. Approximate ED$_{50}$ doses are administered iv bolus and mean arterial pressure (MAP) is recorded every 30 seconds for 5 minutes, then every minute for a 15–20 minute period or until pressure returns to baseline. Changes in MAP (compared to pretreatment values) are analyzed with a paired t-test.

Hypotensive Activity in Normotensive Rats.

Normotensive Sprague-Dawley rats (weighing 400 to 500 g) are anesthetized with 100 mg/kg barbital/25 mg/kg pentobarbital intraperitoneally. The jugular vein and carotid artery are then cannulated with polyethylene-50 tubing (for drug administration and blood pressure measurement, respectively). A tracheotomy tube is inserted and animals breath 100% O$_2$ spontaneously. Also, body temperature is maintained at 37° C. with a thermister probe and heat lamp. After a 10 to 15 minute stabilization period, bolus, i.v. injections of compound are given and responses (decrease in mean arterial pressure in mm Hg) are recorded. A linear regression analysis is then performed on the data to yield the following information:

ED$_0$-threshold dose or dose at which an effect is first observed.

ED$_{50}$-the dose which causes 50% of the maximal response slope of the regression line in mm Hg.

When blood pressure lowering effects are minimal, an ED$_{50}$ cannot be determined and, instead, an ED$_{25}$ (dose which lowers the maximal pressure 25 mm Hg) is calculated.

Utilizing the foregoing test procedures, certain of the preferred embodiments of the compounds of the present invention along with comparison compounds were tested for platelet anti-aggegatory activity and hypotensive activity. The data obtained are set forth in Table I.

TABLE I

| Compound | Anti-Aggregatory | | Blood Pressure |
| | In vitro (ADP-Aggregation) IC$_{50}$ (M) | In vivo (ADP-Thrombocytopenia) ED$_{50}$ (μg/kg/min) | Hexamethonium Rat Blood Pressure/dose (decrease mm/Hg) |
| --- | --- | --- | --- |
| (5S,15S) | $1.0 \times 10^{-7}$ | 2.3 | −42 (10 μg/kg) |
| 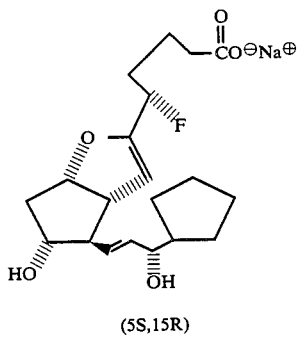 (5S,15R) | $8.6 \times 10^{-6}$ | 3.3 | Inactive (100 μg/kg) |

TABLE I-continued

| Compound | Anti-Aggregatory | | Blood Pressure |
|---|---|---|---|
| | In vitro (ADP-Aggregation) $IC_{50}$ (M) | In vivo (ADP-Thrombocytopenia) $ED_{50}$ (μg/kg/min) | Hexamethonium Rat Blood Pressure/dose (decrease mm/Hg) |
| (5R,15S) | $1.9 \times 10^{-7}$ | 3.0 | −47 (10 μg/kg) |
| (5R,15R) | $6.0 \times 10^{-7}$ | 2.3 | —[1] |
| (15R) | $6.3 \times 10^{-7}$ | — | −76 (100 μg/kg) |
| (5F,15S) | $1.1 \times 10^{-8}$ | 0.87 | −104 (10 μg/kg) |

TABLE I-continued

| | Anti-Aggregatory | | Blood Pressure |
| Compound | In vitro (ADP-Aggregation) $IC_{50}$ (M) | In vivo (ADP-Thrombocytopenia) $ED_{50}$ (μg/kg/min) | Hexamethonium Rat Blood Pressure/dose (decrease mm/Hg) |
| --- | --- | --- | --- |
| 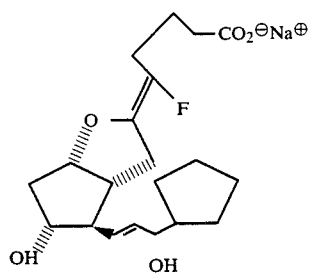 (15S) | $7.6 \times 10^{-8}$ | — | −83 (0.2 μg/kg) |
| 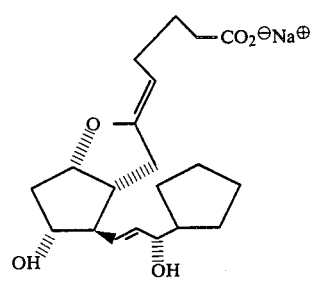 | | | |

1 = not tested.

In order to demonstrate the outstanding separation of properties with respect to anti-aggregatory activity compared to hypotensive activity, a comparison of these activities, was conducted in vivo to obtain the relative therapeutic indices of the 15(R), 15(S) epimers of otherwise structurally identical compounds. The results are set forth in Table II.

TABLE II

| Compound | Anti-Aggregatory in vivo (ADP-Thrombocytopenia) $ED_{50}$ (μg/kg/min) | Blood Pressure $ED_{25}$ (μg/kg) | Therapeutic Index Blood Pressure $ED_{25}$ Anti-Aggregatory |
| --- | --- | --- | --- |
| (5R,15S) | 3.0 | 2.6 | 0.87 |
| 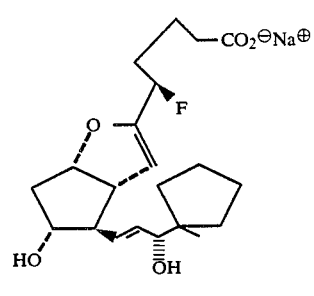 (5R,15R) | 2.3 | 501 | 217.8 |
| 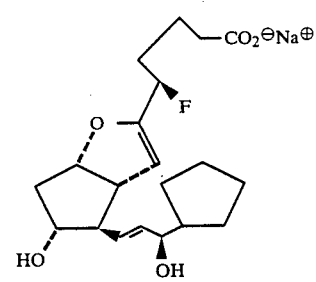 | | | |

From the foregoing, it is evident that the 15(R) derivatives in accordance with the present invention have a therapeutic index heretofore unattainable with natural, i.e., 15(S) prostacyclin derivatives.

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A platelet anti-aggegatory compound selected from at least one compound of the formula:

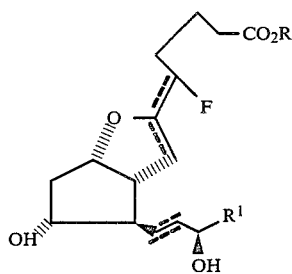

wherein R represents hydrogen, lower alkyl, or a pharmaceutically acceptable cation;

R$^1$ represents a cycloalkyl group of 3 to 7 carbon atoms; and

The symbol ═══ between the 5-, 6-, and 7-positions indicates that a single or double bond exists between either the 5- and 6-positions or the 6- and 7-positions; and the symbol ═══ between the 13- and 14- positions indicates that a single, double, or triple bond exists between the 13- and 14-positions.

2. A compound according to claim 1 wherein the double bond is between the 5- and 6-positions.

3. A compound according to claim 2 of the formula:

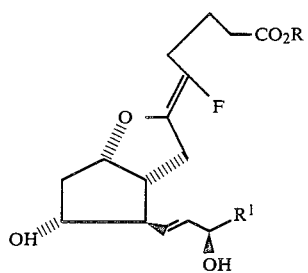

4. A compound according to claim 1 wherein the double bond is between the 6- and 7-positions.

5. A compound according to claim 4 of the formula:

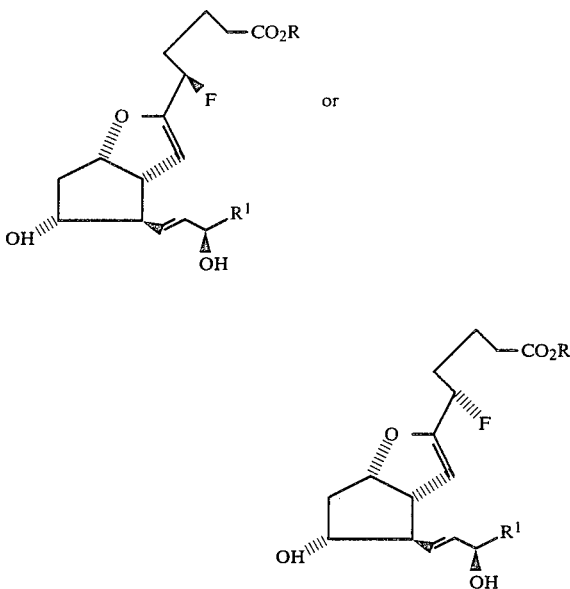

6. A compound according to claim 1 wherein R represents a pharmaceutically acceptable salt selected from the group consisting of Na$^+$, K$^+$, Ca$^{++}$, and quaternary ammonium salts.

7. A compound according to claim 6 wherein said salt is Na$^+$.

8. A compound according to claim 1 wherein said cycloalkyl group is cyclopentyl.

9. A compound according to claim 1 wherein said compound is of the formula:

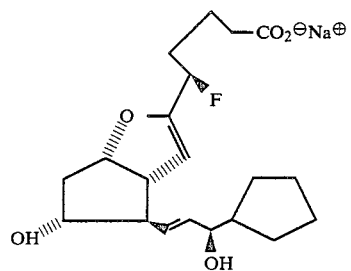

10. A platelet anti-aggregatory pharmaceutical composition comprising an effective platelet anti-aggegatory non-toxic amount of at least one compound according to claim 1 in combination with a pharmaceutically acceptable carrier.

11. A pharmaceutical composition according to claim 10 wherein said compound is of the formula:

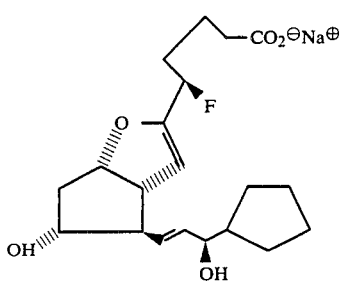

12. A method of promoting a platelet anti-aggregatory effect in a mammal in need thereof comprising administering thereto an effective platelet anti-aggegatory non-toxic amount of at least one compound according to claim 1.

13. A method according to claim 12 wherein said compound is of the formula:

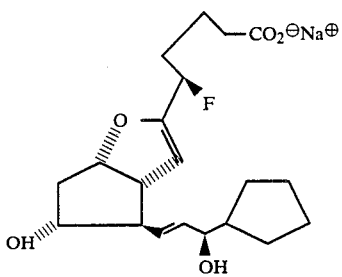

14. A platelet anti-aggregatory compound selected from at least one compound of the formula:

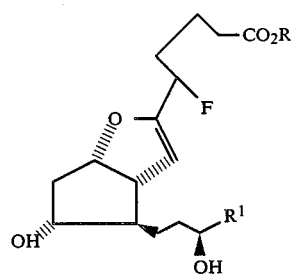

wherein R represents hydrogen, lower alkyl, or a pharmaceutically acceptable cation;

R' represents a straight or branched chain alkyl group of 1 to 5 carbon atoms optionally containing 1 or 2 double bonds or 1 ethynyl group; and The symbol between the 13- and 14-positions indicates that a single, double or triple bond exists between the 13- and 14-positions.

15. A compound according to claim 14 wherein R represents a pharmaceutically acceptable salt selected from the group consisting of Na+, K+, Ca++ and quaternary ammonium salts.

16. A compound according to claim 15 wherein said salt is Na+.

17. A compound according to claim 14 wherein said compound is of the formula:

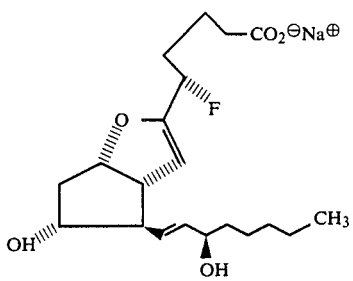

18. A platelet anti-aggregatory pharmaceutical composition comprising an effective platelet anti-aggregatory non-toxic amount of at least one compound according to claim 14 in combination with a pharmaceutically acceptable carrier.

19. A pharmaceutical composition according to claim 18 wherein said compound is of the formula:

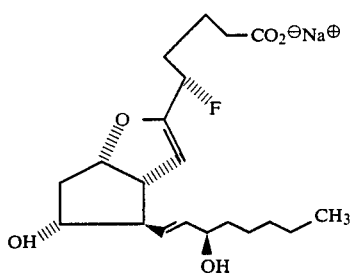

20. A method of promoting a platelet anti-aggregatory effect in a mammal in need thereof comprising administering thereto an effective platelet anti-aggregatory non-toxic amount of at least one compound according to claim 14.

* * * * *